US00PP29031P3

(12) United States Plant Patent
Danziger

(10) Patent No.: US PP29,031 P3
(45) Date of Patent: Feb. 27, 2018

(54) ***COREOPSIS* PLANT NAMED 'DCORGLOW'**

(50) Latin Name: *Coreopsis grandiflora*
Varietal Denomination: DCORGLOW

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 4 days.

(21) Appl. No.: 14/999,368

(22) Filed: Apr. 29, 2016

(65) Prior Publication Data

US 2017/0318722 P1 Nov. 2, 2017

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

PUBLICATIONS

Garden Center Magazine Jul. 2015 Plant Spotlight: Solanna Glow, retrieved on Jun. 22, 2017, retrieved from the Internet at <http://www.gardencentermag.com/article/garden0715-solanna-glow-coreopsis-hybrid/> 3 pp.*

Upov Pluto Plant Variety Database 20170620 for *Coreopsis* 'Dcorglow' retrieved on Jun. 22, 2017, retrieved from the Internet at <http://www.upov.int/pluto/en/index.jsp> 1 page.*

Les Serres Frank Zyromski, Inc. 2015-2016 Net Pricing Unrooted Cuttings from HMA Plants, retrieved on Jun. 22, 2017, retrieved from the Internet at <http://www.zyromski.com/media/wysiwyg/pdf/SFZ_Bdc_2015-16-_HMA.pdf> pp. 1, 4, 17.*

* cited by examiner

*Primary Examiner* — June Hwu
(74) *Attorney, Agent, or Firm* — Cassandra Bright

(57) ABSTRACT

A new and distinct *Coreopsis* cultivar named 'DCORGLOW' is disclosed, characterized by a compact, radial plant habit and dense branching. Flowers are distinctively light, bright yellow. The new variety is a *Coreopsis*, normally produced as an outdoor garden or container plant.

2 Drawing Sheets

Figure 1:
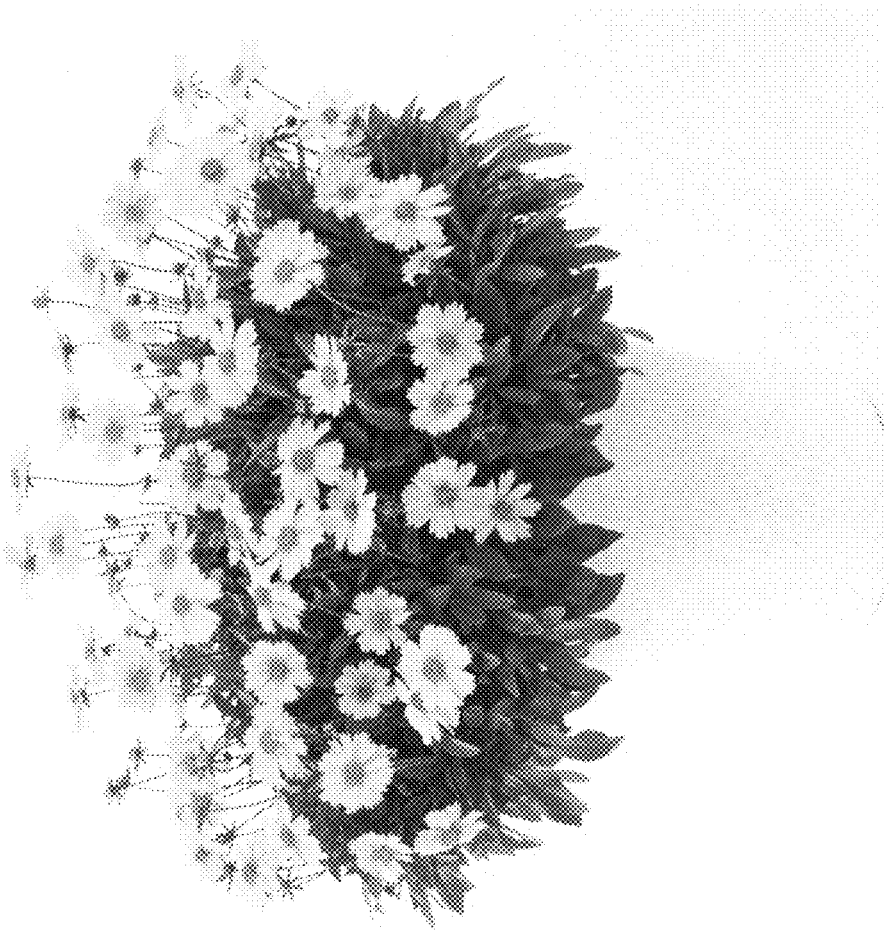

Latin name of the genus and species: *Coreopsis grandiflora.*

Variety denomination: 'DCORGLOW'.

BACKGROUND OF THE INVENTION

The new *Coreopsis* cultivar is a product of a planned breeding program conducted by the inventor, Gavriel Danziger in Moshav Mishmar Hashiva, Israel. The objective of the breeding program was to produce new *Coreopsis* varieties. The open pollination resulting in this new variety was made during June of 2011.

The seed parent is the unpatented, propriety variety referred to as *Coreopsis* 'CO 11-948'. The pollen parent is unknown as it was an open pollination breeding program. The new variety was discovered in July of 2012 by the inventor in a group of seedlings resulting from the 2012 crossing, in a greenhouse in Moshav Mishmar Hashiva, Israel.

Asexual reproduction of the new cultivar 'DCORGLOW' was first performed by terminal vegetative cuttings during September of 2012, at a greenhouse in Moshav Mishmar Hashiva, Israel. Subsequent propagation by vegetative cuttings has shown that the unique features of this cultivar are stable and reproduced true to type in more than 20 successive generations.

SUMMARY OF THE INVENTION

The cultivar 'DCORGLOW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCORGLOW' These characteristics in combination distinguish 'DCORGLOW' as a new and distinct *Coreopsis* cultivar:

1. Distinctive bright light yellow flower color
2. Compact plant habit.
3. Very uniform radial plant shape.
4. Full, dense plant.

PARENT COMPARISON

Plants of the new cultivar 'DCORGLOW' are similar to plants of the seed parent, most horticultural characteristics, however, plants of the new cultivar 'DCORGLOW' differ in the following;

1. Plant habit of the new variety is compact and found, the seed parent is an upright plant.
2. New variety is shorter than the seed parent.
3. Plant structure of the new variety is uniformly radial, plant structure of the seed parent amorphous.
4. Larger flowers than the seed parent.
5. Shorter peduncles than the seed parent.

COMMERCIAL COMPARISON

Plants of the new cultivar 'DCORGLOW' can be compared to the patented commercial variety *Coreopsis*

'DECOREO16' U.S. Plant Pat. No. 25,241. These varieties are similar in most horticultural characteristics; however, 'DCORGLOW' differs in the following:

1. The new variety has a lighter yellow flower than this comparator.
2. The new variety has lighter colored foliage than this comparator.
3. Flowers of the new variety are single, flowers of this comparator are double.
4. Peduncles of the new variety are thinner than peduncles of this comparator.

Plants of the new cultivar 'DCORGLOW' can also be compared to the patented commercial variety *Coreopsis* 'Galaxy' U.S. Plant Pat. No. 21,999. These varieties are similar in most horticultural characteristics; however, 'DCORGLOW' differs in the following:

1. Flowers of the new variety are single, flowers of this comparator are semi-double.
2. Flower color of the new variety is solid light yellow, flower color of this comparator is a blend of yellow and darker yellow.
3. Plant height of the new variety is 20 to 25 cm, this comparator plant height is 25 to 30 cm.

BRIEF DESCRIPTION OF THE PHOTOGRAPHS

The accompanying photograph in FIG. 1 illustrates in full color a typical plant of 'DCORGLOW' grown in 12 cm pots outdoors in Moshav Mishmar Hashiva, Israel.

Figure 2:
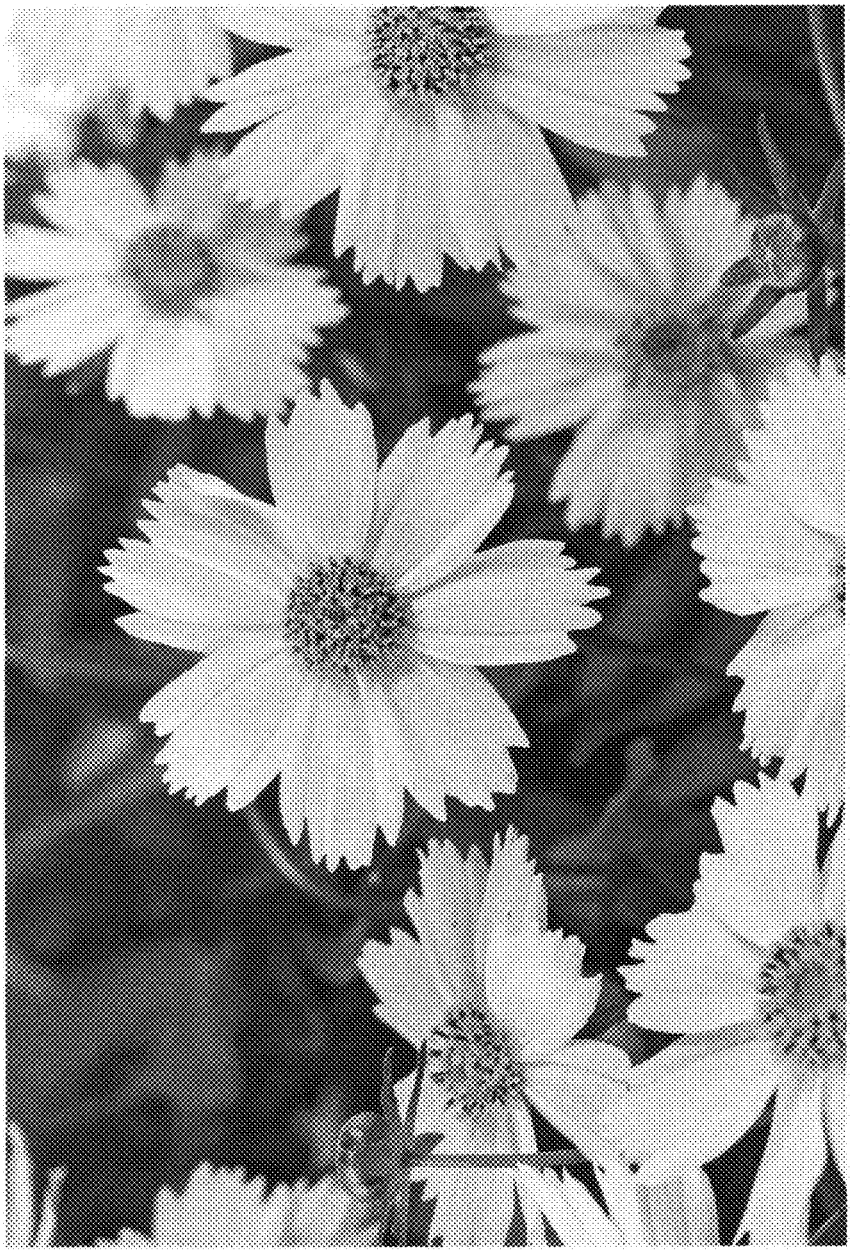

FIG. 2 illustrates in full color multiple typical inflorescence of 'DCORGLOW'. Age of the plant photographed is approximately 11 weeks from a rooted cutting in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCORGLOW' plants grown in a greenhouse in Moshav Mishmar Hashiva, Israel, under natural lighting. Measurements were taken during April of 2016. The plants were approximately 11 weeks old from a rooted cutting in a 12 cm pot. The growing temperature ranged from approximately 18° C. to 28° C. during the days, 13° C. to 18° C. during the nights. Measurements and numerical values represent averages of typical plant types.

Botanical classification: *Coreopsis grandiflora* 'DCORGLOW'.

PROPAGATION

Time to initiate rooting: Summer: 3 to 4 days at approximately 25° C. Winter: 4 to 5 days at approximately 25° C.

Total rooting time: About 14 days at approximately 25° C. for a fully rooted cutting.

Root description: Well branched. Fleshy and white, color not accurately measured with R.H.S. chart.

PLANT

Growth habit: Mounded.
Height: Approximately 20 to 25 cm.
Plant spread: Approximately 25 cm.
Growth rate: Moderate.
Branching characteristics: Well branched, basal branching.
Length of lateral branches: Approximately 12 cm.
Diameter of lateral branches: Approximately 0.3 cm.
Texture of lateral branches: Glossy with very light and delicate hair, slightly ribbed longwise.
Internodes length: Approximately 3.5 cm.
Strength of stem: Flexible and strong, not likely to break.
Color of lateral branches: Near Yellow-Green group 144B.
Aspect/angle of branches: Straight, occurring at approximately 45 degree from ground level.
Number of leaves per lateral branch: Approximately 15.

FOLIAGE

Leaf:
- *Arrangement*.—Sub opposite or whorled from base.
- *Average length*.—Approximately 5 to 7 cm.
- *Average width*.—Approximately 2.5 cm.
- *Shape of blade*.—Oblanceolate.
- *Apex*.—Acute.
- *Base*.—Acuminate.
- *Attachment*.—Petiolate.
- *Margin*.—Entire.
- *Texture of top surface*.—Very light and delicate hair.
- *Texture of bottom surface*.—Very light and delicate hair.
- *Appearance top surface*.—Matte.
- *Appearance bottom surface*.—Slightly metallic.
- *Color*.—Young foliage upper side: Near Green 137B. Young foliage under side: Near Yellow-green 147C. Mature foliage upper side: Near Green 137A. Mature foliage under side: Near Yellow-Green 148B.
- *Venation*.—Type: Reticulate. Venation color upper side: Near Green N137A. Venation color under side: Near Green N137A.

Petiole:
- *Length*.—2.5 cm.
- *Diameter*.—0.2 cm.
- *Pubescence*.—Very light and delicate hair.
- *Color*.—Near Yellow-Green 144A.

FLOWER

Bloom period: In moderate climate zones, USDA Zone 7 and up blooming occurs from Spring to late Fall. In cooler climate zones from Summer until Fall.

Bud:
- *Bud shape*.—Oblate.
- *Bud length*.—Approximately 0.7 cm.
- *Bud diameter*.—Approximately 1.0 cm.
- *Bud color*.—The bud is bi-color forming alternate stripes near Yellow-Green 147A and Yellow-Green 153A.

Inflorescence:
- *Form*.—Composite, single occurring.
- *Lastingness*.—Individual flowers last approximately 5 to 12 days, depending on environmental conditions.

Flower:

*Diameter of entire flower*.—Approximately 6 cm.

*Depth of flower*.—Approximately 1 cm.

*Diameter of disc*.—Approximately 1 cm.

*Depth of disc*.—Approximately 0.5 cm.

Ray florets:

*Number of ray florets*.—8 Avg.

*Length*.—Approximately 2 cm.

*Width*.—Approximately 2 cm.

*Apex shape*.—Praemorse.

*Margin*.—Entire.

Color:

*Ray florets*.—Upper surface at first opening: Near Yellow 4A. Upper surface at maturity: Near Yellow 4B. Upper surface at fading: Near Yellow 4C. Under surface at first opening: Near Yellow 3A. Under surface at maturity: Near Yellow 4A. Under surface at fading: Near Yellow 4B.

Disc florets:

*Number of disc florets*.—Approximately 180.

*Length*.—Approximately 0.8 cm.

*Width*.—Approximately 0.2 cm.

*Shape*.—Tubular with 5 lobes on tip.

*Margin*.—Entire.

*Color*.—At first opening: Near Yellow-Orange 17A. At maturity: Near Yellow-Orange 15A. At fading: Near Yellow-Orange 22A.

Fragrance: Very delicate, sweet scent.

Outer/involucral bracts:

*Number*.—Approximately 8.

*Sepal length*.—Approximately 1.2 cm.

*Sepal width*.—Approximately 0.4 cm.

*Sepal texture*.—Ribbed longwise, stiff and glossy (like plastic).

*Apex shape*.—Acute.

*Margin*.—Entire.

*Color*.—Near Green 137B.

Peduncle:

*Peduncle length*.—Approximately 10 cm.

*Peduncle diameter*.—Approximately 0.2 cm.

*Angle*.—Approximately 90 degree from center of whorl.

*Color*.—Near Yellow-Green 144A.

*Strength*.—Flexible.

*Peduncle texture*.—Glabrous, shiny and slightly ribbed longwise.

REPRODUCTIVE ORGANS

Disc florets:

*Androecium*.—Present, Androecium of 5 stamens, these fused by their anthers, surrounding the style. Stamens: Present, quantity of 5 per floret. Anther shape: Linear and flat. Anther length: Approximately 0.25 cm. Anther color: Near Greyed-Purple 187A. Pollen quantity: Moderate.

*Gynoecium*.—Present, ovary inferior, gynoecium of two fused carpels. Pistil number: 1 per floret. Pistil shape: Cylindrical oblong tube with two branched at tip. Pistil length: Approx. 0.55 cm. Style length: Approx. 0.3 cm. Style color: Near Yellow-Green 145D. Stigma shape: V shaped with two, curved downward, branched-at tip. Stigma color: Near Orange N25D. Ovary Length: 0.2 cm. Ovary color: Near Yellow-Green 149B.

Ray florets: No reproductive structures present.

OTHER CHARACTERISTICS

Seeds and fruits: Achene. Moderate quantity observed. Colored near Grey-Brown 199A. Approximately 4 mm long and 1.5 mm wide.

Disease/pest resistance: Typical to known *Coreopsis* varieties. Neither resistance nor susceptibility to the normal diseases and pests of *Coreopsis* have been observed. Pests common to *Coreopsis* include Aphids and thrips. Typical diseases are *Botrytis* and *Pythium*.

Temperature tolerance: To USDA Zone 5.

Other tolerance: Tolerant to hot, humid Summer climates.

What is claimed is:

1. A new and distinct cultivar of *Coreopsis* plant named 'DCORGLOW' as herein illustrated and described.

* * * * *